US012646615B2

(12) United States Patent
Peake

(10) Patent No.: US 12,646,615 B2
(45) Date of Patent: Jun. 2, 2026

(54) SYSTEMS AND METHODS FOR PASSIVE MONITORING OF A MOBILE DEVICE FOR IDENTIFYING TREATMENT CANDIDATES

(71) Applicant: ResMed Inc., San Diego, CA (US)

(72) Inventor: Gregory Robert Peake, Sydney (AU)

(73) Assignee: ResMed Inc., San Diego, CA (US)

( * ) Notice: Subject to any disclaimer, the term of this patent is extended or adjusted under 35 U.S.C. 154(b) by 840 days.

(21) Appl. No.: 17/629,640

(22) PCT Filed: Jul. 24, 2020

(86) PCT No.: PCT/US2020/043549
§ 371 (c)(1),
(2) Date: Jan. 24, 2022

(87) PCT Pub. No.: WO2021/021650
PCT Pub. Date: Feb. 4, 2021

(65) Prior Publication Data
US 2022/0246293 A1    Aug. 4, 2022

Related U.S. Application Data

(60) Provisional application No. 62/880,860, filed on Jul. 31, 2019.

(51) Int. Cl.
*G16H 40/67* (2018.01)
*G16H 20/30* (2018.01)

(52) U.S. Cl.
CPC ............. *G16H 40/67* (2018.01); *G16H 20/30* (2018.01)

(58) Field of Classification Search
CPC ........ G16H 40/67; G16H 20/30; G16H 50/20; A61B 5/4818; A61B 5/11; A61B 5/4806; A61M 16/00

(Continued)

(56) References Cited

U.S. PATENT DOCUMENTS 10,953,192 B2 *  3/2021  Levendowski ........ A61B 5/369
11,367,519 B1 *  6/2022  Heldman ............... G16H 40/63
(Continued)

FOREIGN PATENT DOCUMENTS

CN      108471988 A     8/2018
EP         3019073 B1 *  8/2022   ............. G16H 50/20
(Continued)

OTHER PUBLICATIONS

Thomee et al., Mobile phone use and stress, sleep disturbances, and symptoms of depression among young adults—a prospective cohort study, BMC Public Health 2011, 11:66, 11 pages (Year: 2011).*

(Continued)

*Primary Examiner* — Jason S Tiedeman
(74) *Attorney, Agent, or Firm* — Nixon Peabody LLP

(57) ABSTRACT

A mobile device for identifying a potential candidate includes a screen, a sensor, and a control system. The sensor configured to generate sensor data associated with use of the mobile device. The control system is configured to: extract location data from the sensor data, the location data including physical location of the mobile device at different time intervals; determine from the location data whether mobility of the mobile device is below a threshold; extract mobile device usage data from the sensor data; determine, from the mobile device usage data, a pattern of use of the mobile device to obtain a sleeping pattern of the potential candidate; and based at least in part on the mobility of the mobile device being below a threshold and the pattern of use of the mobile device, cause the screen to display an alert.

20 Claims, 2 Drawing Sheets

(58) Field of Classification Search
USPC ........................................................ 705/2, 3
See application file for complete search history.

(56) References Cited

U.S. PATENT DOCUMENTS

| | | | | |
|---|---|---|---|---|
| 2006/0185673 | A1* | 8/2006 | Critzer | A61F 2/00 |
| | | | | 128/204.23 |
| 2010/0240982 | A1* | 9/2010 | Westbrook | A61B 5/4818 |
| | | | | 600/538 |
| 2013/0190903 | A1* | 7/2013 | Balakrishnan | G09B 19/003 |
| | | | | 700/91 |
| 2013/0297536 | A1* | 11/2013 | Almosni | G16H 50/20 |
| | | | | 706/12 |
| 2014/0101611 | A1* | 4/2014 | Lang | G06F 3/04842 |
| | | | | 709/204 |
| 2014/0114889 | A1 | 4/2014 | Dagum | |
| 2014/0156084 | A1* | 6/2014 | Rahman | G16H 40/67 |
| | | | | 700/275 |
| 2014/0171146 | A1* | 6/2014 | Ma | G04G 21/04 |
| | | | | 455/550.1 |
| 2014/0258208 | A1* | 9/2014 | Landers | G06N 5/048 |
| | | | | 706/52 |
| 2015/0058263 | A1* | 2/2015 | Landers | G06N 20/00 |
| | | | | 706/11 |
| 2015/0081060 | A1 | 3/2015 | Hwang et al. | |
| 2015/0153374 | A1* | 6/2015 | Balakrishnan | A63B 24/0062 |
| | | | | 702/178 |
| 2015/0154380 | A1* | 6/2015 | Duckworth | G16H 20/30 |
| | | | | 705/2 |
| 2015/0169844 | A1* | 6/2015 | Munafo | A61M 39/22 |
| | | | | 705/2 |
| 2015/0173670 | A1 | 6/2015 | Simon | |
| 2015/0253327 | A1 | 9/2015 | Laidlaw et al. | |
| 2015/0313529 | A1* | 11/2015 | Nevo | A61B 5/4809 |
| | | | | 600/595 |
| 2015/0320588 | A1* | 11/2015 | Connor | F24F 11/0001 |
| | | | | 607/104 |
| 2016/0007934 | A1* | 1/2016 | Arnold | A61B 5/1118 |
| | | | | 600/595 |
| 2016/0151603 | A1* | 6/2016 | Shouldice | A61B 5/486 |
| | | | | 600/26 |
| 2016/0262681 | A1 | 9/2016 | Patterson et al. | |
| 2017/0189641 | A1* | 7/2017 | Moturu | G16H 40/67 |
| 2017/0262606 | A1* | 9/2017 | Abdullah | G16Z 99/00 |
| 2017/0347923 | A1* | 12/2017 | Roh | A61B 5/6831 |
| 2018/0244288 | A1* | 8/2018 | Glaser | B60W 50/14 |
| 2018/0286520 | A1* | 10/2018 | Apte | G16H 50/70 |
| 2018/0330115 | A1* | 11/2018 | Felton | G16H 10/60 |
| 2019/0053754 | A1* | 2/2019 | Gowda | A61B 5/4815 |
| 2019/0160251 | A1* | 5/2019 | Shanmugam | A61M 21/02 |
| 2021/0150873 | A1* | 5/2021 | Shouldice | G06F 21/32 |
| 2021/0375465 | A1* | 12/2021 | Levy | G16H 20/70 |

FOREIGN PATENT DOCUMENTS

| | | | |
|---|---|---|---|
| JP | 2008252798 A | 10/2008 | |
| JP | 2016187429 A | 11/2016 | |
| JP | 2018511363 A | 4/2018 | |
| WO | WO-2015054134 A1 * | 4/2016 | ............ G16H 50/20 |

OTHER PUBLICATIONS

Sawyer et al., Is Inconsistent Pre-treatment Bedtime Related to CPAP Non-Adherence? Res Nurs Health. Dec. 2014 ; 37(6): 504-511 (Year: 2014).*

International Search Report in International Patent Application No. PCT/US2020/043549 mailed Oct. 9, 2020 (4 pp.).

Written Opinion in International Patent Application No. PCT/US2020/043549 mailed Oct. 9, 2020 (7 pp.).

Abdullah S., et al., "Towards circadian computing", Pervasive and Ubiquitous Computing, ACM, 2 Penn Plaza, Suite 701 New York NY, 10121-0701; Seattle WA, USA; Sep. 13, 2014, pp. 673-684.

* cited by examiner

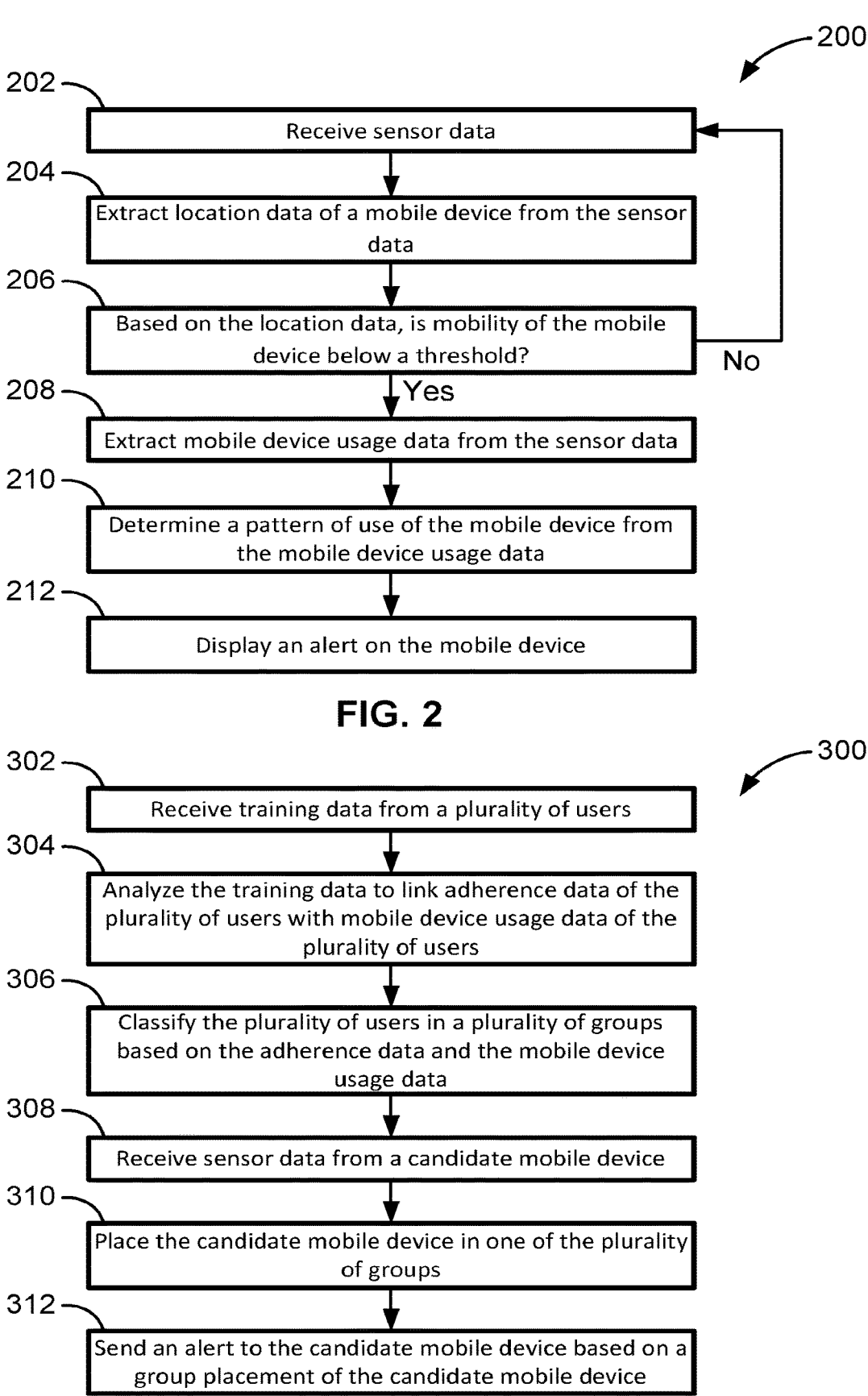

200

202 — Receive sensor data

204 — Extract location data of a mobile device from the sensor data

206 — Based on the location data, is mobility of the mobile device below a threshold?

No

Yes

208 — Extract mobile device usage data from the sensor data

210 — Determine a pattern of use of the mobile device from the mobile device usage data 212 — Display an alert on the mobile device

302 — Receive training data from a plurality of users

304 — Analyze the training data to link adherence data of the plurality of users with mobile device usage data of the plurality of users 306 — Classify the plurality of users in a plurality of groups based on the adherence data and the mobile device usage data 308 — Receive sensor data from a candidate mobile device 310 — Place the candidate mobile device in one of the plurality of groups 312 — Send an alert to the candidate mobile device based on a group placement of the candidate mobile device

FIG. 3

SYSTEMS AND METHODS FOR PASSIVE MONITORING OF A MOBILE DEVICE FOR IDENTIFYING TREATMENT CANDIDATES

CROSS-REFERENCE TO RELATED APPLICATIONS

This application is a U.S. National Stage of International Application No. PCT/US2020/043549, filed Jul. 24, 2020, which claims the benefit of and priority to U.S. Provisional Application No. 62/880,860, filed Jul. 31, 2019, which is hereby incorporated by reference herein in its entirety.

TECHNICAL FIELD

The present disclosure relates to respiratory-related disorders and more specifically to systems and methods for identifying candidates that can benefit from treatments of respiratory-related disorder.

BACKGROUND

Various systems exist for aiding users experiencing sleep apnea and related respiratory disorders. A range of respiratory disorders exist that can impact users. Certain disorders are characterized by particular events (e.g., apneas, hypopneas, hyperpneas, or any combination thereof). Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), and Chest wall disorders. A person with respiratory disorder can have trouble sleeping, and oftentimes, the person is unaware they have a respiratory disorder or that they can benefit from treatments geared at correcting respiratory disorders.

Thus, a need exists for identifying and alerting individuals to potential treatments for respiratory disorders. The present disclosure is directed to solving these problems and addressing other needs.

SUMMARY

According to some implementations, the disclosure provides a method including receiving sensor data from a mobile device associated with a potential candidate. Location data of the mobile device is extracted from the sensor data. The location data includes physical location of the mobile device at different time intervals. A determination of whether mobility of the mobile device is below a threshold is made based on the location data. Mobile device usage data is extracted from the sensor data. From the mobile device usage data, a pattern of use of the mobile device is determined to obtain a sleeping pattern of the potential candidate. An alert to be displayed on a screen of the mobile device is sent to the mobile device. The alert is sent based at least in part on (i) the mobility of the mobile device being below a threshold and (ii) the pattern of use of the mobile device.

According to some implementations, the disclosure provides a method including receiving, from a sensor, sensor data associated with use of a mobile device. Location data is extracted from the sensor data. The location data includes physical location of the mobile device at different time intervals. From the location data, a determination is made on whether mobility of the mobile device is below a threshold. Mobile device usage data is extracted from the sensor data. A pattern of use of the mobile device is determined from the mobile device usage data in order to obtain a sleeping pattern of a potential candidate associated with the mobile device. Based at least in part on the mobility of the mobile device being below a threshold and the pattern of use of the mobile device, a screen of the mobile device is caused to display an alert.

According to some implementations, the disclosure provides a mobile device for identifying a potential candidate. The mobile device includes a screen, a sensor, a memory, and a control system. The sensor configured to generate sensor data associated with use of the mobile device. The memory is configured to store machine-readable instructions. The control system includes one or more processors configured to execute the machine-readable instructions to: extract location data from the sensor data, the location data including physical location of the mobile device at different time intervals, determine from the location data whether mobility of the mobile device is below a threshold, extract mobile device usage data from the sensor data, determine, from the mobile device usage data, a pattern of use of the mobile device to obtain a sleeping pattern of the potential candidate, and based at least in part on the mobility of the mobile device being below a threshold and the pattern of use of the mobile device, cause the screen to display an alert.

According to some implementations, the disclosure provides a non-transitory computer readable medium for identifying a potential candidate. The non-transitory computer readable medium stores instructions thereon such that when executed, causes a server to perform receive sensor data from a mobile device. The server is caused to extract, from the sensor data, location data of the mobile device, the location data including physical location of the mobile device at different time intervals. The server is caused to determine from the location data whether mobility of the mobile device is below a threshold. The server is caused to extract, from the sensor data, mobile device usage data. The server is caused to determine, from the mobile device usage data, a pattern of use of the mobile device to obtain a sleeping pattern of the potential candidate. The server is caused to, based at least in part on the mobility of the mobile device being below a threshold and the pattern of use of the mobile device, send, to the mobile device, an alert for displaying on a screen of the mobile device.

BRIEF DESCRIPTION OF THE DRAWINGS

The foregoing and other advantages of the present disclosure will become apparent upon reading the following detailed description and upon reference to the drawings.

FIG. 2 is a flow diagram for alerting potential candidates with respiratory disorders according to some implementations of the present disclosure; and FIG. 3 is a flow diagram for identifying certain candidates based on similarities with other users according to some implementations of the present disclosure.

Figure 1:
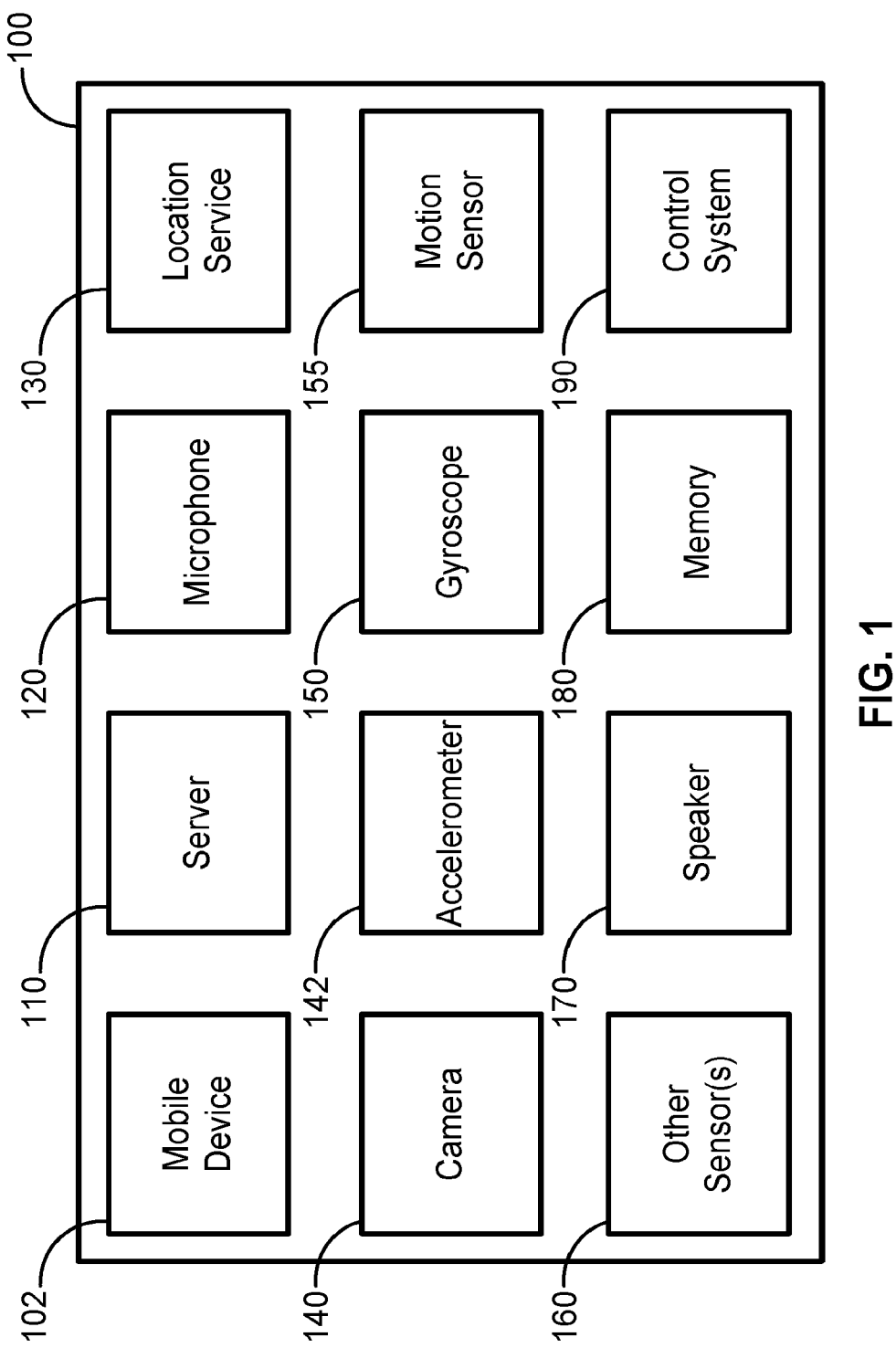
FIG. 1 is a block diagram of a system for identifying and alerting potential candidates with respiratory disorders according to some implementations of the present disclosure.

While the present disclosure is susceptible to various modifications and alternative forms, specific implementations have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

Some implementations of the disclosure screen and identify potential high-risk candidates who may benefit from treatment of a respiratory disorder (e.g., OSA). A candidate can undergo OSA treatment via a continuous positive airway pressure (CPAP) machine used to increase air pressure in the throat of the patient to prevent the airway from closing and/or narrowing during sleep. For a candidate suffering from OSA, her airway can narrow or collapse during sleep, reducing oxygen intake, and forcing her to wake up and/or otherwise disrupt her sleep. The CPAP machine aids in preventing the airway from narrowing or collapsing, thus minimizing the occurrences where she wakes up or is otherwise disturbed (e.g., due to reduction in oxygen intake, choking, coughing, snoring, etc. or any combination thereof).

Some implementations of the disclosure screen and identify potential high-risk candidates who may benefit from treatment of a respiratory disorder and who are likely to comply long-term with the treatment. Treatment of the respiratory disorder may not always be convenient to an individual. For example, a new user of a CPAP machine can develop an initial resistance to a disturbance of her nightly sleep routines for accommodating for the CPAP machine. The user will have to remember to use the machine whenever she is going to sleep, and depending on habit patterns, age, and so on, she may not adhere to using the CPAP machine regularly during a time period (e.g., a month, a year, two years, and so on). As such, in some implementations, the disclosure analyzes datasets generated from a population of CPAP machine users or respirator device users to identify candidates who are likely to comply long-term with treatment.

Individuals are known to have more than one personal electronic device. For example, an individual may have a smartphone, a smart TV, a smartwatch, a connected home security system, and so on. These personal electronic devices can be in communication with each other, allowing a pattern or routine of the individual to be determined. For example, the individual's mobile phone can serve as a hub to aggregate data from all other personal electronic devices of the individual. The individual can rely on the mobile phone for everyday life such that the mobile phone is mostly always within reach of the individual. In some implementations, mobile phone data obtained and analyzed can provide information on whether the individual is a candidate who is likely to comply to a respiratory condition treatment and/or whether the individual is a high-risk candidate who will benefit from a respiratory condition treatment.

Referring to FIG. 1, a block diagram of a system 100 for identifying and alerting potential candidates with respiratory disorders is shown according to some implementations of the present disclosure. The system 100 can include a mobile device 102, a server 110, a microphone 120, a location service 130, a camera 140, an accelerometer 142, a gyroscope 150, a motion sensor 155, other sensor(s) 160, a speaker 170, a memory 180, and a control system 190. To simplify discussion, the singular form will be used for all components identified in FIG. 1 when appropriate, but the use of the singular does not limit the discussion to only one of each such component.

The mobile device 102 is a computing device with a processor and/or memory for executing instructions to perform one or more functions. The mobile device 102 can be a smartphone of a potential candidate, or in some implementations, a combination of a smartphone of the potential candidate and one or more internet of things (IoT) devices or personal electronics of the potential candidate. IoT devices and personal electronics include, for example, smartwatches, room/home thermostats, home security systems, and so on. That is, the mobile device 102 can be two or more devices in communication with one another configured to determine a potential candidate for treatment. The mobile device 102 can analyze data for identifying and alerting potential candidates according to some implementations of the disclosure.

The server 110 is a computing device with a process and/or memory for executing instructions to perform one or more functions. The server 110 can be at a remote location and can be configured to receive information from the mobile device 102. Examples of the server 110 include server computers, computers organized in a cluster, computers in a datacenter, and so on. The server 110 can analyze data for identifying and alerting potential candidates according to some implementations of the present disclosure.

The system 100 can include the microphone 120 for sensing sound in its vicinity. In some implementations, the microphone 120 can be embedded in the mobile device 102, embedded in a smart speaker of the potential candidate, or located anywhere in the room of the potential candidate. When the microphone 120 is not embedded in the mobile device 120, sound data generated by the microphone 120 can be wirelessly communicated to the mobile device 120. For example, a smart speaker can listen for sounds in a room, sending generated sound data to the server 110 for analysis and storage, and the mobile device 102 can retrieve the generated sound data. The microphone 120 can listen for sounds for determining whether the potential candidate is awake or asleep.

The system 100 can include the location service 110. The location service 110 is a system for determining location of the potential user via the mobile device 102. The location service 110 can be a global positioning service (GPS) receiver embedded in the mobile device 102. In some embodiments, the location service 110 can be a geolocation service, such as, for example, a Wi-Fi positioning system (WPS) that uses characteristics of nearby Wi-Fi hotspots and/or other wireless access points to discover where the mobile device 102 is located. The location service 110 can be an indoor positioning service that uses lights, radio waves, magnetic fields, acoustic signals, and so on, to determine the location of the mobile device 102. The mobile device 102 can include one or more radio transmitters and receivers (network interfaces) to support location services that use radio waves, such as, for example, WPS, Bluetooth, and so on. The location of the mobile device 102 can serve as a proxy to the location of the potential candidate.

The system 100 can further include the camera 140. The camera 140 can be embedded in the mobile device 102. The camera 140 can also be located in various parts of a room of the potential candidate and can be configured to communicate video data to the mobile device 102 and/or the server 110. The camera 140 can be used to detect ambient light in its environment. The camera 140 can be used as a light sensor to determine whether the potential candidate has turned on a light in the room. Light being turned off at a certain time of day can indicate that the potential candidate is close to going to sleep.

The system 100 can further include the accelerometer 142. The accelerometer 142 can be embedded in the mobile device 102 and can be configured to generate acceleration data for determining whether the potential candidate is using the mobile device 102. Movement of the mobile device 102 can indicate that the candidate is awake.

The system 100 can further include the gyroscope 150. The gyroscope 150 can be embedded in the mobile device 102 and can be configured to generate orientation data for determining whether the potential candidate is using the mobile device 102. The mobile device 102 changing orientation can be indicative of the candidate being awake.

The system 100 can further include the motion sensor 155. The motion sensor 155 can be embedded in the mobile device 102 and can be configured to generate movement data associated with the potential user. For example, the motion sensor 155 can be a radar sensor utilizing radio waves for mapping a vicinity where the mobile device 102 is located. The radar sensor can use radio wave transmitters and receivers, for example, transmitters and receivers that operate in high frequency band, very high frequency band, long wave, short wave, and so on. The radar sensor can be used to detect whether the potential candidate is moving. The movement data generated by the motion sensor 155 can be indicative of the candidate being awake. The system can further include other sensors 160 (e.g., infrared sensors for determining whether the potential candidate is close to the mobile device 102).

The system 100 can further include the speaker 170. The speaker 170 can be used alongside the microphone 120 to act as a sonar sensor. The speaker 170 can produce sound at intervals, and the microphone 120 can be used to listen for echoes of the sound when the speaker 170 is not producing sound. That way, the microphone 120 and the speaker 170 can be used to detect movement of the potential candidate. The movement indicating whether the potential candidate is awake or asleep.

The memory 180 can include one or more physically separate memory devices, such that one or more memory devices can be coupled to and/or built into the mobile device 102, the control system 190, and/or the server 110 wirelessly coupled and/or wired to the system 100. The memory 180 acts as a non-transitory computer readable storage medium on which is stored machine-readable instructions that can be executed by the control system 190 and/or one or more other systems. The memory 180 is also able to store (temporarily and/or permanently) the data generated by sensors of the system 100. In some implementations, the memory 180 includes non-volatile memory, battery powered static RAM, volatile RAM, EEPROM memory, NAND flash memory, or any combination thereof. In some implementations, the memory 180 is a removable form of memory (e.g., a memory card).

Like the memory 180, the control system 190 can be coupled to the mobile device 102 and/or the server 110. The control system 190 is coupled to the memory 180 such that the control system 190 is configured to execute the machine-readable instructions stored in the memory 180. The control system 190 can include one or more processors and/or one or more controllers.

In some implementations, the control system 190 is a dedicated electronic circuit. In some implementations, the control system 190 is an application-specific integrated circuit. In some implementations, the control system 190 includes discrete electronic components.

The control system 190 is able to receive input(s) (e.g., signals, generated data, instructions, etc.) from any of the other elements of the system 100 (e.g., the sensors, etc.). The control system 190 is able to provide output signal(s) to cause one or more actions to occur in the system 100 (e.g., to cause the mobile device 102 to display an alert to the potential candidate). The control system 190 can be located in the mobile device 102 and/or the server 110 and/or elsewhere in the system 100.

Referring to FIG. 2, a flow diagram for alerting potential candidates with respiratory disorders is shown according to some implementations of the present disclosure. At step 202, the control system 190 (and/or the mobile device 102 and/or the server 110 in some implementations) receives sensor data. The sensor data can pertain to a certain time period, for example, the sensor data can be data accumulated by different sensors of the system 100 for half a day, a day, two days, a week, a month, and so on. The sensor data can include location data determined via the location service 130. The sensor data can include accelerometer data and movement data determined via, for example, the accelerometer 142, the gyroscope 150, the motion sensor 155, and so on. The sensor data can be obtained from sensors of the mobile device 102 or any sensors of the system 100 as described in connection with FIG. 1.

At step 204, the control system 190 (and/or mobile device 102 and/or the server 110 in some implementations) extracts location data of the mobile device 102 from the received sensor data. The location data can include physical location of the mobile device 102 at different timestamps. At step 206, the control system 190 (and/or the mobile device 102 and/or the server 110 in some implementations) determines, based on the extracted location data, whether mobility of the mobile device 102 is below a threshold.

Mobility of the mobile device 102 can include total distance traveled by the mobile device 102 which can indicate a total distance walked and/or ran by the owner of the mobile device 102 within a time period. Mobility of the mobile device 102 can include a total number of location changes of the mobile device 102 within a time period, such as, within an hour, two hours, a day, a week, and so on. The total number of location changes being below a certain threshold can indicate whether that the owner of the mobile device 102 has a sedentary lifestyle. A sedentary lifestyle can imply the owner may suffer from obesity which is correlated with respiratory disorders. Location can be measured in one or more levels of granularity, including, for example, different areas within a room, different rooms within a house/complex, different houses/complexes, and so on. Location can also be measured in a regular or irregular grid of a map, with the grid defining the granularity.

In some implementations, the location data is analyzed to determine whether the mobile device 102 is moving too quickly. When the mobile device 102 is moving too quickly, for example, greater than 15 miles per hour, the location data indicates that the mobile device 102 is in a vehicle. When the mobile device 102 is determined to be in a vehicle, then the mobility of the mobile device 102 is not taken into consideration.

In some implementations, mobility of the mobile device 102 is generally taken as a proxy for body movements of the user of the mobile device 102. Hence any movement of the mobile device 102 determined not to be primarily driven by a body movement is not taken into consideration. For example, the user of the mobile device 102 can be on a bike moving very quickly. After determining that the mobile device 102 is moving too quickly, other sensor data can be used in a further analysis to determine whether the user is exerting herself through body movements. Examples of sensor data that can be used in the further analysis include orientation data from the gyroscope 150, sound data from the microphone 120, acceleration data from the accelerometer 142, and so on.

In some implementations, the location data is analyzed to determine whether the mobile device 102 is moving at a walking pace, for example, less than four miles per hour. The location data can also indicate whether the mobile device 102 is moving at a running pace, for example, between four miles per hour and twelve miles per hour. The location data can also be analyzed to determine a distance covered by the mobile device 102. In some implementations, the distance covered by the mobile device can be compared to a distance threshold to characterize mobility. In some implementations, pace of movement of the mobile device 102 can be compared to a speed threshold to characterize mobility.

In some implementations, for example, the mobile device 102 can move at twelve miles per hour but only cover a distance of 0.12 miles. In another example, the mobile device 102 can move at four miles per hour but cover a distance of four miles. The 0.12 miles can be determined to be below a distance threshold so mobility of the mobile device is determined to be below the threshold. On the other hand, four miles can be determined to be above the distance threshold so mobility of the mobile device is determined to be above the threshold.

In some implementations, although the 0.12 miles is below the distance threshold, twelve miles per hour can be determined to be above the speed threshold. That is, when the mobile device can sustain a certain speed for a minimum duration, even though the distance threshold may not be met, the speed threshold can be met. In some implementations, meeting the speed threshold along with meeting the minimum duration can be regarded as the mobility of the mobile device 102 being above the threshold.

In some implementations, after using the location data, the location data can be sent to the server 110 and/or an external memory for storage. The location data can then be deleted from the mobile device 102. That way, storage solutions and security of the location data can be enhanced, preventing other users or other applications running on the mobile device 102 to access the location data. If the mobile device 102 (and/or the control system 190 in some implementations) needs access to the location data, the mobile device 102 can retrieve the location data from the server 110 and/or the external memory.

A potential candidate that cannot sustain a certain minimum speed for a minimum time can be inferred to have a respiratory condition. In some implementations, the respiratory condition may be preventing the candidate from exerting more effort. A potential candidate that does not move a minimum distance during a day can be inferred to have a respiratory condition. The respiratory condition may be preventing the candidate from going on walks, runs, and so on. At step 206, mobility of the mobile device 102 is characterized to determine whether the mobility is below the threshold. The mobility of the mobile device 102 serves as a proxy to movement or mobility of the potential candidate, such that a candidate with limited mobility is more likely to be a candidate suitable for treatment of a respiratory condition.

At step 208, the control system 190 (and/or mobile device 102 and/or the server 110 in some implementations) extracts mobile device usage data from the sensor data. The mobile device usage data includes data that indicates that a potential candidate is using the mobile device 102. Movement data and orientation data obtained from sensors of the system 100

(e.g., the accelerometer 142, the gyroscope 150, and so on) can indicate that the potential candidate has moved the mobile device 102.

Draining battery life of the mobile device 102 at a rate higher than a drain rate during a sleep state of the mobile device 102 can be included in the mobile device usage data and can indicate the potential candidate is using the mobile device 102. The screen of the mobile device 102 being ON can be included in the mobile device usage data and can indicate that the potential candidate is using the mobile device 102. Receiving touch inputs and/or voice commands at the mobile device 102 can be included in the mobile device usage data and can indicate that the potential candidate is using the mobile device 102. When the speaker 170 is integrated in the mobile device, and the mobile device 102 plays music or sound via the speaker 170, the information can be included in the mobile device usage data.

At step 210, the control system 190 determines a pattern of use of the mobile device 102 from the mobile device usage data. In some implementations, the mobile device usage data includes timestamps for a beginning and an end of when the mobile device 102 is being. That way, the mobile device usage data can indicate intervals or periods of use of the mobile device 102 and intervals or periods of non-use of the mobile device 102.

The periods of use and/or the periods of non-use of the mobile device 102 can be used to approximate a sleeping pattern of the potential candidate. In some implementations, the periods of non-use exceeding a certain time interval are taken as periods where the potential candidate is asleep. In some implementations, the periods of non-use occurring at specific times of the day are taken as periods where the potential candidate is asleep. For example, the potential candidate may work during the day and sleep at night, therefore, periods of non-use at night-time longer than a certain interval, for example, thirty minutes, forty-five minutes, one hour, two hours, three hours, and so on, are determined as periods where the potential candidate is asleep. In another example, the potential candidate may work during the night and sleep during the day, therefore, periods of non-use during day-time longer than a certain interval are determined as periods where the potential candidate is asleep.

In some implementations, the control system 190 observes multiple days of the mobile device usage data to determine the sleeping pattern of the potential candidate. Over multiple days, the control system 190 can determine whether the potential candidate primarily sleeps during day-time or primarily sleeps during night-time. The control system 190 can then determine whether the potential candidate goes to sleep around the same time of day on most days. The control system 190 can set a margin around a sleep time, for example, an hour margin, a thirty-minute margin, a twenty-minute margin, a ten-minute margin, and so on. The control system 190 can then determine how many periods of non-use begin within the margin around the sleep time. If the number of periods of non-use exceeds a certain number of days, the control system 190 can determine that the potential candidate goes to bed around a certain time.

In some implementations, start times and end times for each of the periods of non-use can be corrected using additional sensor data. For example, for a night-time sleeper, ambient light captured by the camera can be used to adjust a period of non-use to account for when light was turned off in the room. Rate of battery drain on the mobile device 102 can be used to determine whether to adjust start and/or end times of a period of non-use. The potential candidate may be playing and/or streaming music, so rate of battery drain can be used to determine that the potential candidate is not asleep.

In some implementations, sound data generated by the microphone 120 can be used to adjust a period of non-use to account for when the potential user is talking, listening to music, watching television, and so on.

In some implementations, the sensor data and the mobile device usage data include screen data. The screen data indicates periods where the screen of the mobile device 102 is ON, that is, screen-on intervals. The control system 190 can use the screen data to determine screen-on intervals and a time of day when each screen-on interval began. The screen-on interval can be used to adjust start times and/or end times of periods of non-use. The screen-on interval can also be used to determine periods of non-use.

A regular sleep time being kept by a potential candidate can indicate that the potential candidate is rigorous in keeping a bed-time pattern and/or ritual. A potential candidate with a regular bed-time pattern and/or ritual can be found to be more likely a candidate that will comply long-term with a treatment for a respiratory condition.

In some implementations, an individual that regularly goes to bed before 8:30 PM but wakes up around 7 AM indicates that the individual does not sleep well. In some implementations, the control system determines that multiple screen-on intervals observed starting at night-time, e.g., between 10 PM and 6 AM, can indicate that the individual is waking multiple times throughout the night and is not sleeping well. Brief interruptions in periods of non-use can be determined to indicate that the individual is waking multiple times during a sleep session.

At step 212, the control system 190 (and/or the server 110 in some implementations) can cause the mobile device 102 to display an alert based at least in part on the mobility of the mobile device 102 being below the threshold and the pattern of use of the mobile device. Based on the pattern of use of the mobile device showing a regular bed-time pattern, the control system 190 can cause the mobile device 102 to display the alert. Based on periods of non-use and adjusted periods of non-use as described elsewhere in this disclosure in relation to step 210, the control system 190 can cause the mobile device 102 to display the alert.

In some implementations, the alert displayed by the mobile device 102 includes a request for a sex or gender of the potential candidate, a request for an age of the potential candidate, a request for a sleep quality of the potential candidate, a request for a body mass index (BMI) of the potential candidate, or any combination thereof.

The potential candidate can provide answers to the different requests provided in the alert. The potential candidate can use input interface(s) of the mobile device 102 to provide the answers. The provided answers can be denoted as environmental inputs from the potential candidate. In some implementations, answers to the requests made of the potential candidate in the alert can be obtained from one or more databases. And the alert is provided to the potential candidate so that the potential candidate can confirm whether the obtained answers from the one or more databases is correct.

In some implementations, based on the environmental inputs from the potential candidate, the control system 190 causes the mobile device 102 to display an invitation. The invitation is used to ask the potential candidate whether she is willing to undergo treatment for a respiratory condition. For example, the invitation can ask the potential candidate whether she will undergo a treatment with a CPAP machine.

Referring to FIG. 3, a flow diagram for identifying certain candidates based on similarities with other users is shown according to some implementations of the present disclosure. At step 302, the control system 190 (and/or the server 110 in some implementations) receives training data from a plurality of users. Training data from each user can include sensor data (as described elsewhere in connection with FIGS. 1 and 2) generated from mobile devices, CPAP machines, and/or other sensors or devices of the plurality of users. Each of the plurality of users is a user that is undergoing or has previously undergone treatment for a respiratory condition. The training data can be used to train a machine learning algorithm. The training data can be an aggregation of statistical data from the plurality of users over a time period.

At step 304, the control system 190 (and/or the server 110 in some implementations) analyzes the training data to link adherence data of the plurality of users with mobile device usage data of the plurality of users. The training data can include adherence data which describes compliance of each of the plurality of users with the treatment of their respective respiratory condition. Adherence data can be obtained from an app on a mobile device of a user. For example, the mobile device of the user can indicate times when a CPAP machine was turned ON by the user. The mobile device of the user can indicate how many respiratory incidents that the CPAP machine measured while ON. Adherence data can also include location data obtained from the mobile device to determine that the CPAP data obtained and the location of the user's home and/or bedroom match.

Mobile device usage data is described elsewhere in connection with FIG. 2. Mobile device usage data of each of the plurality of users can be used by the control system 190 to determine usage patterns and features. The control system 190 can use a machine learning algorithm to determine the features and to link the adherence data to the mobile device usage data.

At step 306, the control system 190 can classify the plurality of users in a plurality of groups based on the adherence data and the mobile device usage data. The control system 190 can bin or cluster users in the plurality of users into groups. For example, the control system 190 can determine that the plurality of users fall into two separate groups: low risk candidate and high risk candidate. The control system 190 can determine that the plurality of users fall into three separate groups: low risk candidate, medium risk candidate, and high risk candidate. The plurality of groups can further include: low risk candidate with low compliance, low risk candidate with high compliance, medium risk candidate with low compliance, medium risk candidate with high compliance, high risk candidate with low compliance, and high risk candidate with high compliance.

Features such as age, compliance, gender, and severity of respiratory condition can be used to classify the plurality of users into the plurality of groups. For example, a female user aged between eighteen and thirty years old, suffering a mild respiratory condition, but using her CPAP machine thirty-five percent of the time she sleeps, can be classified as a medium risk candidate with a low compliance rate. A male user aged between forty and fifty years old, suffering from a more severe respiratory condition, but using his CPAP machine sixty-nine percent of the time she sleeps, can be classified as a high risk candidate with a medium compliance rate. A female user aged between sixty and seventy years old, suffering from a very severe respiratory condition, and using his CPAP machine eighty-five percent of the time she sleeps, can be classified as a high risk candidate with a high compliance rate. At step 306, the control system 390 groups users based on compliance and physiological attributes. The control system can use a machine learning algorithm to determine the number of groups and/or to determine which users fall within each of the groups.

At step 308, the control system 190 receives sensor data from a candidate mobile device. The candidate mobile device can be, for example, the mobile device 102. Step 308 is similar to step 202 of FIG. 2. Types of sensor data that can be received are discussed elsewhere in connection with FIGS. 1 and 2.

At step 310, the control system 190 places the candidate mobile device in one of the plurality of groups introduced at step 306. Based on the received sensor data, the control system 190 can compare the received sensor data with training data (or aggregate statistical data) obtained from the plurality of users in step 302. The control system 190 can then determine that the candidate mobile device is more similar to certain users in one of the plurality of groups and places the candidate mobile device as belonging in that group.

At step 312, the control system 190 can send an alert to the candidate mobile device based on a group placement of the candidate mobile device. For example, if the candidate mobile device is placed in a group indicating high risk and high compliance, then the control system 190 can send an alert to the candidate mobile device so that the candidate mobile device displays the alert on its screen. The alert can take a form as described elsewhere in connection with FIG. 2.

In some implementations, the disclosure utilizes a correlation between phone usage data, sleep data, and/or mobility patterns to selectively identify individuals who are at risk of a respiratory condition (e.g., OSA) and would likely fall in a long-term compliance bucket. In some implementations, users who tend to sleep early and have lower mobility would likely fall in the long-term adherence bucket to therapy.

While the present disclosure has been described with reference to one or more particular implementations, those skilled in the art will recognize that many changes may be made thereto without departing from the spirit and scope of the present disclosure. Each of these embodiments and implementations and obvious variations thereof is contemplated as falling within the spirit and scope of the present disclosure, which is set forth in the claims that follow.

COMPUTER & HARDWARE IMPLEMENTATION OF DISCLOSURE

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

What is claimed is:

1. A method performed by a control system of a mobile device, the control system including one or more processors and a memory storing instructions, the mobile device associated with a potential candidate for a respiratory condition, the method comprising:

receiving, by the control system, sensor data from sensors of the mobile device, the sensors including at least a global positioning receiver and an accelerometer;

extracting, by the control system, from the sensor data, location data of the mobile device, the location data including physical location of the mobile device at different time intervals;

determining, by the control system and using the location data of the mobile device, a mobility of the mobile device within a time period, the mobility comprising a total distance traveled by the mobile device within the time period, a total number of location changes of the mobile device within the time period, or both;

determining, by the control system and using the location data, whether the mobility of the mobile device is below a threshold;

extracting, by the control system and using the sensor data, mobile device usage data;

determining, by the control system and using the mobile device usage data, a pattern of use of the mobile device to obtain a sleeping pattern of the potential candidate;

determining, by the control system, that the pattern of use of the mobile device indicates at least a plurality of intervals of non-use across multiple days, wherein each of the plurality of intervals of non-use starts within a time margin of a same time of day for the multiple days;

receiving, by the control system and at least one additional sensor of the mobile device, additional sensor data from the mobile device;

adjusting, by the control system, a period of the plurality of intervals of non-use by adjusting the same time of the day based on the additional sensor data, wherein adjusting the period of the plurality of intervals of non-use comprises correcting for (i) ambient light captured by a camera, (ii) battery-drain patterns detected by the control system, and (iii) ambient sounds captured by a microphone to align the plurality of intervals of non-use to the same time of the day within the time margin under varying environmental conditions;

sending, by the control system, an alert for displaying on a screen of the mobile device based on satisfaction of (i) the mobility of the mobile device being below the threshold, and (ii) the pattern of use of the mobile device indicating that the plurality of intervals is aligned to the same time of the day within the time margin as adjusted using the additional sensor data; and responsive to sending the alert, deleting, by the control system, the location data from the mobile device.

2. The method of claim 1, further comprising:

comparing the mobile device usage data to aggregate statistics on usage data of other candidates, the aggregate statistics being linked to adherence data describing therapy compliance of each of the other candidates, wherein sending the alert for displaying on the screen is further based at least in part on results of the comparison.

3. The method of claim 1, further comprising:
receiving, from the mobile device, environmental inputs of the potential candidate; and
sending, to the mobile device, an invite based on the environmental inputs, wherein the environmental inputs indicate a sex of the potential candidate, an age of the potential candidate, a sleep quality of the potential candidate, or any combination thereof.

4. The method of claim 1, further comprising:
extracting, from the sensor data, screen data comprising one or more screen-on intervals and a time of day when each screen-on interval begins, wherein sending the alert for displaying on the screen is further based at least in part on the time of day when each screen-on interval begins.

5. A method performed by a control system of a mobile device, the control system including one or more processors and a memory storing instructions, the mobile device associated with a potential candidate for a respiratory condition, the method, comprising:
receiving, by the control system from a sensor, sensor data of the mobile device;
extracting, by the control system, location data from the sensor data, the location data including physical location of the mobile device at different time intervals;
determining, by the control system and using the location data of the mobile device, a mobility of the mobile device within a time period, the mobility comprising a total distance traveled by the mobile device within the time period, a total number of location changes of the mobile device within the time period, or both;
determining, by the control system and using the location data, whether the mobility of the mobile device is below a threshold;
extracting, by the control system, mobile device usage data from the sensor data;
determining, by the control system and using the mobile device usage data, a pattern of use of the mobile device to obtain a sleeping pattern of a potential candidate associated with the mobile device;
determining, by the control system, that the pattern of use of the mobile device indicates at least a plurality of intervals of non-use across multiple days, wherein each of the plurality of intervals of non-use starts within a time margin of a same time of a day for the multiple days;
receiving, by the control system and at least one additional sensor of the mobile device, additional sensor data from an additional sensor on the mobile device;
adjusting, by the control system, a period of the plurality of intervals of non-use by adjusting the same time of the day based on the additional sensor data, wherein adjusting the period of the plurality of intervals of non-use comprises correcting for (i) ambient light captured by a camera, (ii) battery-drain patterns detected by the control system, and (iii) ambient sounds captured by a microphone to align the plurality of intervals of non-use to the same time of the day within the time margin under varying environmental conditions;
sending, by the control system, an alert for displaying on a screen of the mobile device based on satisfaction of (i) the mobility of the mobile device being below the threshold, (ii) the plurality of intervals of non-use of the mobile device is aligned to the same time of the day within the time margin as adjusted using the additional sensor data, and (iii) the potential candidate is likely to comply with long-term treatment of the respiratory disorder using a continuous positive airway pressure (CPAP) machine; and
responsive to sending the alert, deleting, by the control system, the location data from the mobile device.

6. The method of claim 5, further comprising:
receiving aggregate statistics on usage data of other candidates from one or more external servers, the aggregate statistics linked to adherence data describing therapy compliance of each of the other candidates;
comparing the mobile device usage data to the aggregate statistics to predict an adherence of the potential candidate; and
causing the screen to display the alert further based at least in part on results of the comparison.

7. The method of claim 5, wherein the sensor includes an accelerometer configured to generate acceleration data of the mobile device such that the mobile device usage data includes the acceleration data indicating times when the mobile device was moved.

8. The method of claim 5, wherein the sensor includes a global positioning service (GPS) receiver configured to provide the physical location of the mobile device in the location data.

9. The method of claim 5, further comprising:
providing, by a network interface of the mobile device, the physical location of the mobile device in the location data, the network interface supporting Wi-Fi based positioning systems, Bluetooth, or any combination thereof.

10. The method of claim 5, wherein the alert includes a request for a sex of the potential candidate, a request for an age of the potential candidate, a request for a sleep quality of the potential candidate, or any combination thereof.

11. The method of claim 5, further comprising:
receiving environmental inputs from the potential candidate using an input interface; and
causing the screen to display an invite based on the environmental inputs from the potential candidate.

12. The method of claim 5, wherein:
the sensor data includes screen data comprising one or more screen-on intervals and a time of day when each screen-on interval begins; and
causing the screen to display the alert is further based at least in part on the time of day when each screen-on interval begins.

13. A mobile device for identifying a potential candidate, comprising:
a screen;
a sensor configured to generate sensor data associated with use of the mobile device;
a memory storing machine-readable instructions; and
a control system including one or more processors configured to execute the machine-readable instructions to:
extract location data from the sensor data, the location data including physical location of the mobile device at different time intervals,
determine, from the location data of the mobile device extracted from the sensor data, a mobility of the mobile device within a time period, the mobility comprising a total distance traveled by the mobile device within the time period, a total number of location changes of the mobile device within the time period, or both, determine, using the location data, whether mobility of the mobile device is below a threshold, extract mobile device usage data from the sensor data, determine, using the mobile device usage data, a pattern of use of the mobile device to obtain a sleeping pattern of the potential candidate, determine that the pattern of use of the mobile device at least indicates a plurality of intervals of non-use across multiple days, wherein each of the plurality of intervals of non-use starts within a time margin of a same time of a day for the multiple days, receive, from at least one additional sensor of the mobile device, additional sensor data from the mobile device, adjust a period of the plurality of intervals of non-use by adjusting the same time of the day based on the additional sensor data, wherein adjusting the period of the plurality of intervals of non-use comprises correcting for (i) ambient light captured by a camera, (ii) battery-drain patterns detected by the control system, and (iii) ambient sounds captured by a microphone to align the plurality of intervals of non-use to the same time of the day within the time margin under varying environmental conditions, and send an alert for displaying on the screen of the mobile device, based on satisfaction of (i) the mobility of the mobile device being below the threshold, and (ii) the plurality of intervals of non-use of the mobile device is aligned to the same time of the day within the time margin as adjusted using the additional sensor data; and responsive to sending the alert, deleting, by the control system, the location data from the mobile device.

14. The mobile device of claim 13, further comprising:

a network interface configured to communicate with one or more external servers, wherein the control system is further configured to:

receive aggregate statistics on usage data of other candidates from the one or more external servers, the aggregate statistics linked to adherence data describing therapy compliance of each of the other candidates, compare the mobile device usage data to the aggregate statistics to predict an adherence of the potential candidate, and cause the screen to display the alert further based at least in part on results of the comparison.

15. The mobile device of claim 13, wherein the sensor includes an accelerometer configured to generate acceleration data of the mobile device such that the mobile device usage data includes the acceleration data indicating times when the mobile device was moved.

16. The mobile device of claim 13, wherein the sensor includes a global positioning service (GPS) receiver configured to provide the physical location of the mobile device in the location data.

17. The mobile device of claim 13, further comprising:

a network interface configured to provide the physical location of the mobile device in the location data, the network interface supporting Wi-Fi based positioning systems, Bluetooth, or any combination thereof.

18. The mobile device of claim 13, wherein the alert includes a request for a sex of the potential candidate, a request for an age of the potential candidate, a request for a sleep quality of the potential candidate, or any combination thereof.

19. The mobile device of claim 13, further comprising:

an input interface configured to receive environmental inputs from the potential candidate, wherein the control system is further configured to cause the screen to display an invite based on the environmental inputs from the potential candidate.

20. The mobile device of claim 13, wherein:

the sensor data includes screen data comprising one or more screen-on intervals and a time of day when each screen-on interval begins; and the control system is further configured to cause the screen to display the alert further based at least in part the time of day when each screen-on interval begins.

* * * * *